(12) United States Patent
Muehlsteff et al.

(10) Patent No.: US 10,912,467 B2
(45) Date of Patent: Feb. 9, 2021

(54) APPARATUS AND METHOD FOR PROVIDING A CONTROL SIGNAL FOR A BLOOD PRESSURE MEASUREMENT DEVICE

(71) Applicant: KONINKLIJKE PHILIPS N.V., Eindhoven (NL)

(72) Inventors: Jens Muehlsteff, Eindhoven (NL); Erik Bresch, Eindhoven (NL); Teun van den Heuvel, Eindhoven (NL); Lars Schmitt, Eindhoven (NL); Dieter Woehrle, Waiblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 779 days.

(21) Appl. No.: 15/550,915

(22) PCT Filed: Feb. 18, 2016

(86) PCT No.: PCT/EP2016/053484
§ 371 (c)(1),
(2) Date: Aug. 14, 2017

(87) PCT Pub. No.: WO2016/135043
PCT Pub. Date: Sep. 1, 2016

(65) Prior Publication Data
US 2018/0042493 A1  Feb. 15, 2018

(30) Foreign Application Priority Data

Feb. 24, 2015 (EP) ..................................... 15156286

(51) Int. Cl.
*A61B 5/02* (2006.01)
*A61B 5/0225* (2006.01)
(Continued)

(52) U.S. Cl.
CPC .......... *A61B 5/0225* (2013.01); *A61B 5/0006* (2013.01); *A61B 5/021* (2013.01);
(Continued)

(58) Field of Classification Search
CPC .... G16H 50/30; A61B 5/7275; A61B 5/0225; A61B 5/021; A61B 50/30; A61B 5/0006;
(Continued)

(56) References Cited

U.S. PATENT DOCUMENTS 5,606,977 A * 3/1997 Ramsey, III ....... A61B 5/02225
600/494
5,842,996 A * 12/1998 Gruenfeld .......... A61B 5/02233
600/490

(Continued)

FOREIGN PATENT DOCUMENTS

| EP | 0986323 A1 | 3/2000 |
|---|---|---|
| EP | 1127538 A1 | 8/2001 |
| WO | 2013056319 A1 | 4/2013 |

*Primary Examiner* — Christian Jang

(57) ABSTRACT

The present invention relates to an apparatus (18) for providing a control signal for a blood pressure measurement device, comprising: an input interface (24) for obtaining a health state parameter being indicative of a health state of a patient (12); a processing unit (28) for determining one or more operation settings of a blood pressure measurement device (14) based on the health state parameter, said one or more operation settings including a parameter that can be adjusted at the blood pressure measurement device (14) when conducting a blood pressure measurement with the device and that affects a precision of said blood pressure measurement and a patient comfort resulting from said blood pressure measurement; and a control interface (30) for providing a control signal for a blood pressure measurement device (14) to perform a blood pressure measurement based on said one or more operation settings. The present invention further relates to a corresponding method. Still further, (Continued)

the present invention relates to a system for monitoring a patient.

15 Claims, 8 Drawing Sheets

(51) Int. Cl.
  *A61B 5/00* (2006.01)
  *A61B 5/021* (2006.01)
  *G16H 50/30* (2018.01)
  *A61B 5/022* (2006.01)
  *A61B 8/04* (2006.01)

(52) U.S. Cl.
  CPC ........ *A61B 5/02141* (2013.01); *A61B 5/7275* (2013.01); *G16H 50/30* (2018.01); *A61B 5/0024* (2013.01); *A61B 5/02225* (2013.01); *A61B 8/04* (2013.01)

(58) Field of Classification Search
  CPC .............. A61B 5/02141; A61B 5/0024; A61B 5/02225; A61B 8/04; A61B 8/00
  See application file for complete search history.

(56) References Cited

U.S. PATENT DOCUMENTS

| | | | |
|---|---|---|---|
| 6,719,703 | B2 | 4/2004 | Chen et al. |
| 6,805,670 | B2 | 10/2004 | Shirasaki |
| 2001/0012916 | A1 | 8/2001 | Deuter |
| 2007/0232867 | A1 | 10/2007 | Hansmann |
| 2008/0235058 | A1 | 9/2008 | Friedman et al. |
| 2010/0324429 | A1* | 12/2010 | Leschinsky .......... A61B 17/135 600/493 |
| 2011/0066045 | A1* | 3/2011 | Moon ................ A61B 5/02125 600/485 |
| 2013/0158417 | A1 | 6/2013 | Borger |
| 2014/0031639 | A1* | 1/2014 | Toyomura ............ A61B 5/0205 600/301 |
| 2014/0249431 | A1* | 9/2014 | Banet .................. A61B 5/0022 600/485 |
| 2014/0249433 | A1 | 9/2014 | Banet et al. |
| 2015/0332012 | A1* | 11/2015 | Edelson ............. A61B 5/02225 600/494 |

* cited by examiner

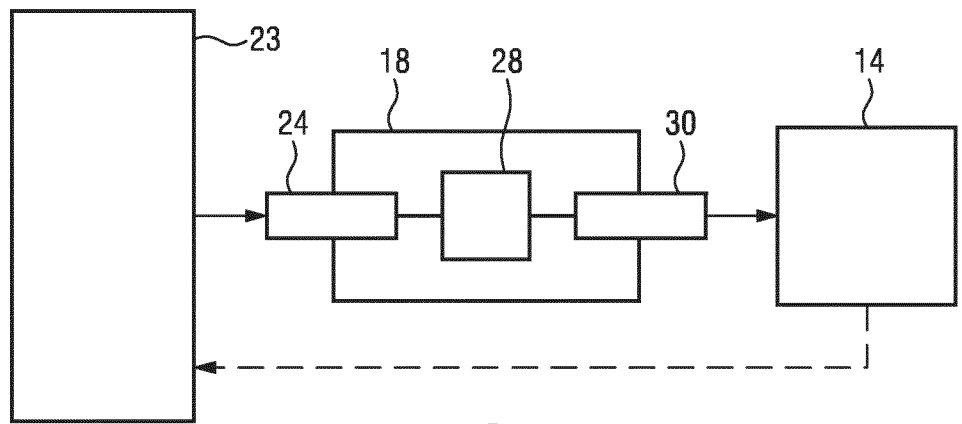
FIG.3
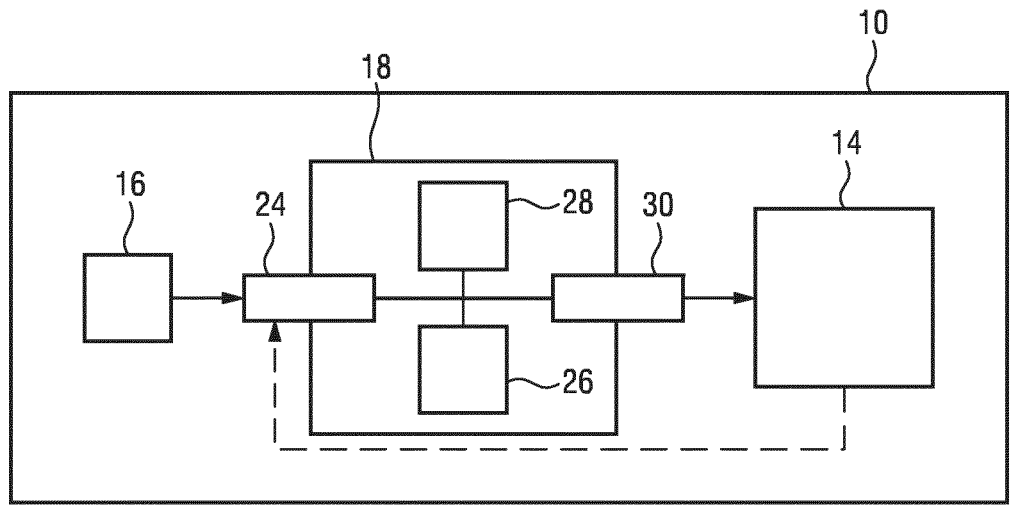
FIG.4
| Score | 3 | 2 | 1 | 0 | 1 | 2 | 3 |
|---|---|---|---|---|---|---|---|
| Heart rate | | <40 | 40-50 | 51-100 | 101-110 | 111-130 | >130 |
| Blood pressure (syst) | <70 | 70-80 | 81-100 | 101-200 | | >200 | |
| Respiratory rate | | <9 | | 9-14 | 15-20 | 21-30 | >30 |
| Temperature | | <35,1 | 35,1-36,5 | 36,6-37,5 | >37,5 | | |
| Awareness | | | | A | V | P | U |
| A = alert  V = response to appeal  P = response to pain  U = no reaction ||||||||
FIG.5

APPARATUS AND METHOD FOR PROVIDING A CONTROL SIGNAL FOR A BLOOD PRESSURE MEASUREMENT DEVICE

This application is the U.S. National Phase application under 35 U.S.C. § 371 of International Application No. PCT/EP2016/053484, filed on Feb. 18, 2016, which claims the benefit of European Application No. 15156286.5, filed Feb. 24, 2015. These applications are hereby incorporated by reference herein.

FIELD OF THE INVENTION

The present invention relates to an apparatus and method for providing a control signal for a blood pressure measurement device. Further, the present invention relates to a system for monitoring a patient.

BACKGROUND OF THE INVENTION

Early recognition of subtle signs of patient deterioration has been seen as one of the major problems to be addressed in different monitoring scenarios. Philips Healthcare offers the Philips Monitor MP5SC for general wards, which acquires SpO2, blood pressure, temperature, and breathing gas CO2. This monitor can be used in spot-check as well as for continuous monitoring purposes.

For automated spot-check monitoring in low acuity it is, e.g., possible to make use of wireless sensors. For instance, an accelerometer at the apex position to detect pulse, respiration as well as posture and activity information of a patient may be combined with a cuff-based blood pressure monitor at the upper arm and a SpO2 sensor at the wrist. These sensors allow spot-check monitoring of a patient's vitals in an automated way at a high level of freedom and comfort.

One important vital sign to be monitored is the blood pressure. Various monitoring approaches for invasively and non-invasively measuring the blood pressure of a patient exist.

Non-invasive blood pressure (NIBP) measurements are mainly based on the sphygmomanometric occlusive arm-cuff, which allows for intermittent measurements only. This methodology may be uncomfortable for the patient, since a limb of the patient is compressed with an external pressure, a procedure which may reduce patient comfort or may even hurt a patient. Automated NIBP measurements originally developed for intensive care units often have a strong emphasis on the accuracy of the measurement and less focus on patient comfort aspects.

It has, e.g., been found in Beltman et al., "Acceptance and Side Effects of Ambulatory Blood Pressure Monitoring", J. Human Hypertension, 1996, that NIBP measurements often have a relatively low acceptance. This is due to side effects such as, pain caused by inflation (duration, peak pressure), irritation of the skin under the cuff, hematomas and/or sleep disturbance. Potential measures to increase the acceptance include reducing the total measurement time, the maximum cuff pressure and/or the integral of the pressure over time.

In US 2001/0012916 A1 a blood pressure measuring device is presented. The device has a pressure cuff the inflation of which is automatically effected and controlled by an evaluation and control unit to allow a continuous monitoring of a patient's blood pressure, especially during the night without infringing the patient's comfort and sleep. The device also includes an ECG device and a sensor for sensing the pressure in the cuff. In a first mode of operation, the control and evaluation unit calculates an estimated blood pressure value from pulse wave transmission times with each calculated pulse wave transmission time being the time elapsing between a heart beat as detected by the ECG device and a corresponding cuff pressure change detected by the pressure sensor. In the event of the appearance of blood pressure spikes while operating in the first mode, the device switches to a second operating mode during which absolute blood pressure values are determined.

There is, however, still a need to improve existing blood pressure measurement approaches as well as monitoring approaches with respect to patient comfort.

In US 2013/0158417 A1 a method, apparatus and computer program for automatic non-invasive blood pressure measurement are disclosed. To improve the specificity of automatic blood pressure determinations in a patient monitor provided with a non-invasive blood pressure determination unit, a physiological index indicatve of sympathetic activity is derived from a subject, variations in the physiological index are monitored, and the blood pressure determination unit is instructed to initiate blood pressure determination when the variations fulfill a predetermined condition.

In EP 1 127 538 A1 an approach to automated blood pressure monitoring is disclosed. An automated sphygmomanometer triggers a blood pressure determination upon detection of a significant change in the patient's heart rate reliability (HRV). The HRV can be measured directly from the NIBP signal or, when a multiparameter monitor is used, the HRV can be measured from the ECG signal of the NIBP signal. HRV is continuously monitored and the baseline HRV is corrected with baseline blood pressure values. Changes in HRV are displayed continuously on the display so that the clinician can determine whether to initiate the NIBP measurement or, on the other hand, the NIBP measurement can be triggered automatically in response to a change in HRV without any intervention by the clinician. Alternatively, the patient monitor can "learn" the correlation between HRV and blood pressure changes and only alert the clinician when a significant change in HRV has taken place.

SUMMARY OF THE INVENTION

It is an object of the present invention to provide an apparatus for providing a control signal for a blood pressure measurement device as well as a corresponding method. It is further an object of the present invention to provide a system for monitoring a patient.

In a first aspect of the present invention an apparatus for providing a control signal for a blood pressure measurement device, comprising: an input interface for obtaining a health state parameter being indicative of a health state of a patient; a processing unit for determining one or more operation settings of a blood pressure measurement device based on the health state parameter, said one or more operation settings including a parameter that can be adjusted at the blood pressure measurement device when conducting a blood pressure measurement with the device and that affects a precision of said blood pressure measurement and a patient comfort resulting from said blood pressure measurement; and a control interface for providing a control signal for a blood pressure measurement device to perform a blood pressure measurement based on said one or more operation settings.

In a further aspect of the present invention a method for providing a control signal for a blood pressure measurement device is presented. The method comprises the steps of obtaining a health state parameter being indicative of a health state of a patient; determining one or more operation settings of a blood pressure measurement device based on the health state parameter, said one or more operation settings including a parameter that can be adjusted at the blood pressure measurement device when conducting a blood pressure measurement with the device and that affects a precision of said blood pressure measurement and a patient comfort resulting from said blood pressure measurement; and providing a control signal for a blood pressure measurement device to perform a blood pressure measurement based on said one or more operation settings.

In another aspect of the present invention a system for monitoring a patient is presented. The system comprises at least one vital sign sensor for providing at least one input signal being indicative of a vital sign of the patient; a health assessment unit for determining a health state parameter being indicative of a health state of the patient based on the at least one input signal; an apparatus as described above; a blood pressure measurement device for conducting a blood pressure measurement on the patient; and a user interface for providing the determined health state parameter and/or a blood pressure of the patient to a user, in particular a physician.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system and computer program and medium have similar and/or identical preferred embodiments as the claimed apparatus and as defined in the dependent claims.

On the one hand, a blood pressure measurement is often uncomfortable for a patient. On the other hand, the maximum precision or accuracy with respect to the measured blood pressure that a blood pressure measurement can provide is not always required in a monitoring scenario as long as the patient's condition is uncritical. Most of the time, it may be sufficient to carry out a measurement of lower precision as long as the patient is of good health. It is only occasionally necessary to perform a measurement of high precision, e.g. when the patient's condition suddenly deteriorates. Then, it may be required to provide very accurate blood pressure measurements to allow the patient or medical personnel to react appropriately.

The present invention is based on the idea of performing a blood pressure measurement based on operation settings for a blood pressure measurement device that represent a trade-off between the precision of the measurement and the patient comfort resulting from a blood pressure measurement. In other words, the operation settings of a blood pressure measurement device are adapted in dependence of a current health state of a patient. Particularly a systolic and/or a diastolic blood pressure is to be measured.

A health state parameter of a patient is obtained, e.g. from a sensor system or from a clinical information system or from an input by a physician or other medical personnel. This health state parameter is indicative of the health state of the patient, i.e. how healthy a patient is or how good his condition is at the moment. Particularly, a health state parameter may be indicative of the well-being of the patient or the severity of a medical condition the patient suffers from. For instance, a health state parameter may be determined based on a vital sign of the patient and/or based on his medical history.

The health state parameter forms the basis for determining one or more operation settings of a blood pressure measurement device. Operation settings of a blood pressure measurement device may refer to any parameters that can be adjusted at the device when conducting a blood pressure measurement. A blood pressure measurement device can be controlled based on operation settings. For instance, it may be possible to adjust parameters such as the measurement frequency, duration, the algorithm based on which a blood pressure measurement is derived from a measured signal, etc. The operation settings depend on the type of blood pressure measurement device that is used. As used herein, operation settings of a blood pressure measurement device particularly refer to adjustable parameters of an automated measurement device. It may, however, also be possible to provide operation settings for a manually operated blood pressure measurement device operated, e.g. by a physician.

Depending on how a blood pressure measurement device is operated, i.e. based on which operation settings, the patient is more or less affected, i.e. the patient comfort being caused by the measurement may be lower or higher. Also, however, the precision of a measurement, i.e. the accuracy or validity with respect to the measured blood pressure, can be affected by the chosen operation settings.

In the context of the present invention, operation settings are particularly relevant if they relate to a precision of the blood pressure measurement on the one hand and to the patient comfort that is caused when a blood pressure measurement is conducted on the other. The chosen operation settings result in a certain measurement precision and a certain patient comfort.

For instance, in the context of a blood pressure measurement conducted by means of a sphygmomanometer, the operation settings may include a maximum pressure applied to a limb of a patient, an integral of the pressure over time, a duration of a measurement, a number of detected heartbeats or combinations of these or other parameters. A patient is disturbed (i.e. his comfort is lower) if a measurement takes too long or if high pressure is applied to his limb. A measurement of a lower frequency during the night might cause less harm (higher comfort). The device can be operated according to these operation settings means that it is possible to choose or select these settings.

According to the present invention it is proposed to determine operation settings of the blood pressure measurement device that are related to both the precision of a blood pressure measurement conducted with the device and the patient comfort resulting from said blood pressure measurement in an optimal fashion. Operation settings are determined in a trade-off between the measurement precision and the patient comfort.

Depending on the health state of the patient it may be required that a measurement of higher or lower precision is performed. On the one hand, the precision of the measurement may be deliberately increased (whereby patient comfort is reduced) if a patient is not doing well and needs to be monitored accurately or constantly. On the other hand, it may also be possible to reduce the precision of the conducted blood pressure measurement if a lower accuracy measurement is appropriate. For instance, if a patient is already on the mend it might not be necessary to measure with a very high measurement frequency and therefrom resulting high accuracy with respect to the measured blood pressure of the patient.

The processing unit may derive the one or more operation settings based on a predefined function or also based on a look-up table or an adapted or adaptive function with or without input from a user and/or physician.

The determined operation settings are then used to control the blood pressure measurement device. A control interface controls the blood pressure measurement device by providing a control signal. On the one hand, it is possible that a blood pressure measurement device is in direct communication with the apparatus of the present invention via the control interface and is controlled in real time according to the determined operation settings. On the other hand, it may also be possible that the control signal is used remotely or at a later point in time.

As used herein, a control signal for a blood pressure measurement device may particularly refer to a signal that can be interpreted by a blood pressure measurement device and that causes the operation settings of the blood pressure measurement device to be set according to the determined operation settings.

In comparison to previous blood pressure measurement device control approaches the present invention allows improving patient comfort by adjusting the accuracy of a blood pressure measurement device or providing a control signal to adjust the accuracy or precision of a blood pressure measurement. It is envisioned to provide operation settings that relate to the minimum required precision (and the maximum possible patient comfort).

In particular, it is interesting to adjust the measurement precision in situations in which a more accurate measurement is not needed. One application area of the present invention are monitoring setups e.g. in general ward facilities. In such settings it is usually only required that blood pressure measurements are reported with a precision sufficient for a hospital-specific Early Warning Scoring (EWS) system with an intended patient risk classification performance. In such scenarios, the present invention proposes an adaptive context-specific measurement precision that allows keeping a similar EWS notification performance at improved patient comfort. For instance, in such a system a higher precision is not required if this higher precision would have no effect on the determined risk score anyway. Thus, a trade-off between measurement precision and patient comfort is obtained.

In a first embodiment of the apparatus as defined above the processing unit is configured to determine one or more operation settings related to a lower precision and a higher patient comfort when the health state parameter indicates an uncritical health state of the patient; and determine one or more operation settings related to a higher precision and a lower patient comfort when the health state parameter indicates a deteriorating health state of the patient. Thus, if the patient is in an uncritical health state, i.e. it is not likely that the condition of the patient deteriorates in the next time, operation settings are determined that are related to a lower precision and higher patient comfort. In other words, if it is determined that the patient is feeling well a control signal is provided that controls the blood pressure measurement device to perform a blood pressure measurement of a lower precision but which causes less harm to the patient, i.e. results in a higher patient comfort. Opposed thereto, if the patient is in a deteriorating health state and it is necessary to monitor the patient with high accuracy it is accepted that the patient is bothered by the blood pressure measurement, i.e. that a blood pressure measurement of higher precision is conducted at the price of lower patient comfort. Thereby, an optimal trade-off between patient comfort and required measurement precision is obtained. The terms "lower and higher precision" particularly define a qualitative relation between the accuracy of a conducted blood pressure measurement with respect to how valid this blood pressure measurement is with respect to the actual blood pressure of a patient.

In another embodiment the input interface is configured to obtain a risk score indicating the health state of the patient on a predefined scale, said risk score being below a predefined threshold indicating an uncritical health state of the patient and said risk score being above said predefined threshold indicating a deteriorating health state of the patient. One possibility of measuring the health state of a patient is by using a risk score on a predefined scale. For instance, the health state of a patient may be indicated on a scale from 1 to 10 with 1 indicating that the patient is very well and that it is very unlikely that the condition of the patient deteriorates in the near future, and 10 indicating that the patient's condition is very critical and it is required to monitor the condition of the patient as accurately as possible to not miss any deterioration in the health state of the patient. It may then be possible that a threshold is defined which distinguishes between an uncritical health state and a deteriorating health state of the patient. Depending on whether or not the risk score is above said threshold, operation settings are determined that relate to a high or low precision and a low or high patient comfort. Such a risk score is often used in EWS systems in hospitals. This embodiment corresponds to a simple control approach for controlling a blood pressure measurement device based on the output of an EWS system.

In yet another embodiment the control interface is configured to provide a control signal for a sphygmomanometer comprising an inflatable cuff for being applied to a limb of the patient and a pressure sensor for providing a pressure signal being indicative of the pressure in the inflatable cuff; and the processing unit is configured to determine one or more operation settings being related to said higher precision and said lower patient comfort by resulting in a systolic blood pressure of the patient being inferred based on a standard method, in particular an auscultatory or oscillometric method, during deflation of the inflatable cuff. One common type of blood pressure measurement device is a sphygmomanometer. The inflatable cuff of this sphygmomanometer can be applied to a limb of a patient such as an arm or a leg or a finger. The blood pressure of the patient can then be derived from a pressure signal being indicative of the pressure in the inflatable cuff. Regularly, such a device is operated based on operation settings that require that the inflatable cuff is inflated to a maximum pressure at which no pulse can pass through the cuff. Then the pressure is slowly decreased to perform the measurement. Different standard methods for determining the blood pressure of a patient from a pressure signal provided by a pressure sensor in an inflatable cuff of a sphygmomanometer during deflation of the inflatable cuff exist. In the auscultatory method usually a stethoscope is used to derive the systolic blood pressure (SBP) as the pressure at which the first Korotkoff sound is heard. The cuff pressure is then released until no sound can be heard (fifth Korotkoff sound) at the diastolic arterial pressure (DBP). Alternatively, the oscillometric method involves the observation of oscillations in the sphygmomanometer cuff pressure which are caused by the oscillations of blood flow, i.e., the pulse. The pressure signal is automatically interpreted and values for the systolic and diastolic blood pressure are obtained. Such a standard method results in a comparably high accuracy.

In an embodiment the control interface is configured to provide a control signal for a sphygmomanometer comprising an inflatable cuff for being applied to a limb of the patient and a pressure sensor for providing a pressure signal being indicative of the pressure in the inflatable cuff; and the processing unit is configured to determine one or more operation settings being related to said lower precision and said higher patient comfort by resulting in a systolic blood pressure of the patient being inferred based on at least one of: extrapolation of a signal envelope of the pressure signal during cuff inflation; extraction of a diastolic blood pressure and a mean arterial blood pressure from a signal envelope of the pressure signal during cuff inflation; and extraction of a diastolic blood pressure from a signal envelope of the pressure signal during cuff inflation and extraction of a mean arterial blood pressure from a vital sign of the patient corresponding to a surrogate blood pressure measurement of the patient, in particular a pulse transit time or a pulse arrival time, derived from at least one additional signal, in particular a photoplethysmography signal and/or an electrocardiogram.

According to this embodiment, one main advantage is that the maximum cuff pressure can be reduced if only a measurement of reduced accuracy (lower precision and higher patient comfort) needs to be conducted. It is possible to obtain an estimate for the systolic blood pressure by extrapolating a signal envelope of the pressure signal during cuff inflation. According to this embodiment, it is possible that cuff inflation is stopped as soon as the obtained blood pressure measurement is considered to be sufficiently accurate. For instance, the cuff may only be inflated for a few seconds until a certain number of heartbeats are detected. The accuracy may be increased if the cuff is inflated for a longer time period. Also, it is possible to extract a diastolic blood pressure and a mean arterial blood pressure from a signal envelope of the pressure signal during cuff inflation as described above. Then, the systolic blood pressure may be calculated based on the relation between the diastolic blood pressure and the mean arterial blood pressure. Again, it is possible to obtain a measurement of higher or lower precision and of lower or higher patient comfort depending on the chosen operation settings of the blood pressure measurement device. Still further, it is possible to extract a diastolic pressure from a signal envelope of the pressure signal during cuff inflation and to extract a mean blood pressure from a vital sign of the patient corresponding to a surrogate blood pressure measurement.

Different vital signs of the patient carry information on the blood pressure of the patient. These are referred to as surrogate blood pressure measurements and allow deriving information related to the mean blood pressure of the patient. Such a surrogate blood pressure measurement may be available from an additional signal obtained from a vital sign sensor being connected to the blood pressure measurement device or being part of a monitoring system. For instance, a pulse transit time or a pulse arrival time derived from an additional signal (e.g. a photoplethysmography signal or an ECG signal) may be used as a surrogate blood pressure measurement. The systolic blood pressure can then be calculated based on the fixed relation between the mean arterial blood pressure, the diastolic blood pressure and the systolic blood pressure. This embodiment is particularly advantageous since it may not be required to fully inflate the cuff and thereby save time and decrease the maximum pressure of a cuff applied to a limb of the patient so that patient comfort is increased.

In a further embodiment the input interface is configured to obtain at least one input signal being indicative of a vital sign of a patient and the apparatus further comprises a health assessment unit for determining a health state parameter being indicative of a health state of the patient based on the at least one input signal. An input signal being indicative of a vital sign of the patient may be obtained in addition to the health state parameter. It may also be possible that the obtained input signal being indicative of a vital sign is considered to represent the health state parameter. The apparatus includes an input interface via which at least one input signal is obtained. Such an input signal may be obtained from a device for measuring a vital sign of a patient. Such an input signal may also be obtained from a database or from an input of medical personnel. Preferably, an input signal refers to a measured parameter over time, which is related to a vital sign of a patient. It is possible that a device for obtaining such an input signal is included in a common housing with the apparatus of the present invention. It is, however, also possible that the input interface is connected to a remote measurement device by wired or wireless connection or also through the internet. It is thereby possible that one signal being indicative of one vital sign of the patient is obtained. It is, however, also possible that multiple signals being indicative of the same vital sign or being indicative of different vital signs are obtained. Based on the obtained at least one input signal a health state parameter is determined in a health assessment unit. To obtain this health parameter the health assessment unit may apply a predefined processing to the obtained at least one input signal. It may also be possible that the applied processing of health assessment unit is adapted based on current requirements or based on user input.

In yet another embodiment the input interface is configured to obtain an input signal from the blood pressure measurement device, said input signal being indicative of a blood pressure of the patient. One of the one or more input signals is thus obtained from the blood pressure measurement device that is controlled via the control interface. For instance, the pressure signal of a sphygmomanometer as described above may represent an input signal. The blood pressure measurement is measured based on operation settings that relate to a certain precision and patient comfort. This measurement is used to obtain the blood pressure of the patient and to derive therefrom information on his health state. Then again, this health state is evaluated to derive therefrom operation settings for conducting a blood pressure measurement. This embodiment thus corresponds to a control loop, i.e. allows obtaining a closed control loop for controlling a blood pressure measurement device.

In another embodiment the input interface is configured to obtain an input signal and a corresponding accuracy indicator, in particular a standard deviation, being indicative of a validity of the input signal with respect to the vital sign, said accuracy indicator being predefined for a respective input signal or being updated continuously based on a current blood pressure measurement. This accuracy indicator may indicate a current validity or significance or explanatory power of the obtained input signal. It may be possible that the accuracy indicator is constant for a specific type of input signal. It may also be possible that the accuracy indicator is continuously updated based on a current blood pressure measurement. It may be possible that a certain measurement has predefined corresponding accuracy indicator value. In a preferred embodiment a standard deviation, in particular an estimated standard deviation can be used as an accuracy indicator. The advantage from the additional use of an accuracy indicator is that it becomes possible to additionally include the validity of the currently received input signal in the considerations when deriving therefrom the current health state of the patient. Thus, the health state of the patient can be assessed with higher accuracy. It becomes possible to determine operation settings as a function of how accurately the current blood pressure measurement is or is considered to be.

In yet another embodiment at least one of the processing unit is configured to determine the one or more operation settings based on said input signal and said corresponding accuracy indicator; and the health assessment unit is configured to determine the health state parameter based on said input signal and said corresponding accuracy indicator. This accuracy indicator may be used in the processing unit for determining the one or more operation settings and/or in the health assessment unit when determining the health state parameter of the patient. Both the calculations and the processing unit and the calculations in the health assessment unit may be carried out with higher significance if additionally the accuracy indicator is considered.

In yet another preferred embodiment the input interface is configured to obtain medical record data of the patient in addition to the at least one input signal, said medical record data being indicative of a medical history of the patient; and the health assessment unit is configured to determine the health state parameter based on the medical record data of the patient in addition to the at least one input signal. If medical record data of the patient are considered in addition to the at least one input signal the health state of the patient may be assessed with a higher significance. Depending on the medical history as summarized in the medical record of a patient, it may be necessary to differently interpret a current measurement of a vital sign of the patient. For instance, a patient may generally have a lower body temperature without this indicating a deteriorating health state. If such information is included in the medical record data it may be possible to consider this information and determine the health state parameter accordingly. The accuracy or significance of the determined health state parameter is thus increased. In particular, medical record data may refer to any data relating to a previous health condition of the patient. Such medical record data may be obtained from a clinical information system or from a physician etc. Medical record data may also relate to parameters such as age, gender, weight etc.

In a preferred embodiment the input interface is configured to obtain an input signal being indicative of a blood pressure, a blood oxygen saturation, a body temperature, a concentration of carbon dioxide in the respiratory gases, a heart rate, a pulse arrival time, a pulse transit time, a pulse morphology and a breathing frequency of the patient. Depending on the underlying algorithm and the application it may be possible to derive the current health state of the patient from a plurality of different input signals being indicative of different vital signs of the patient. It may also be possible that one input signal is indicative of different vital signs or that different input signals are indicative of the same vital sign. In these cases, it may still be advantageous to make use of the different input signals or to determine the different vital signs based on the same input signals to obtain redundancy and/or to increase the accuracy and validity.

In yet another embodiment the input interface is configured to obtain a protocol parameter in addition to the at least one input signal, said protocol parameter being indicative of a predefined treatment policy; and the processing unit is configured to determine the one or more operation settings based on said input signal and said protocol parameter. Such a protocol parameter may be indicative of a treatment policy as specified by a physician or other medical personnel. For instance, a hospital may specify that a certain health state of a patient as derived from a vital sign of this patient requires that the blood pressure of this patient is measured based on certain predefined operation settings. For instance such a protocol parameter may indicate that the measurement frequency for the blood pressure is increased to, e.g., one measurement per 10 minutes, if the systolic blood pressure of the patient is below a certain threshold. Such a protocol parameter may be updated continuously or may be obtained once for a longer time period.

In an embodiment the control interface is configured to provide a control signal for a sphygmomanometer comprising an inflatable cuff for being applied to a limb of the patient and a pressure sensor for providing a pressure signal being indicative of the pressure in the inflatable cuff; and the processing unit is configured to determine one or more operation settings including at least one of a parameter being indicative of a maximum pressure in the inflatable cuff during a measurement, a parameter being indicative of a duration of the inflatable cuff being inflated during a measurement, a parameter being indicative of an intgral of the pressure applied during a measurement and a parameter being indicative of a number of heartbeats to be detected.

As used herein, operation settings may include parameters acting upon a measurement, i.e. defining the properties of a measurement to be conducted. The individual measurement is conducted upon these parameters. The operation setting directly relate to the measurement, i.e. to the configuration of the blood pressure measurement device or, in other words, to the properties of the measurement. Thus, the operation settings have a direct influence on how a measurement is conducted. Usually, the operation settings thereby define how the device is controlled for carrying out each measurement. The operation settings imply a certain patient comfort and a certain measurement precision. Usually, a higher precision implies a lower comfort for the patient. The processing unit determines which measuremet precision is required in the current situation and determines appropriate operation settings. In particular, it may be possible that every measurement of a series of measurements is carried out based on different and individually determined operation settings. Every measurment in the series is thus as comfortable as possible for the patient and has a sufficient precision for the current situation.

BRIEF DESCRIPTION OF THE DRAWINGS

These and other aspects of the invention will be apparent from and elucidated with reference to the embodiment(s) described hereinafter. In the following drawings

FIG. 3 shows a schematic illustration of an embodiment of an apparatus for providing a control signal for a blood pressure measurement device according to an aspect of the present invention;

FIG. 4 shows a schematic illustration of another embodiment of an apparatus according to the present invention;

FIG. 5 shows an example for an early warning system scoring card;

DETAILED DESCRIPTION OF THE INVENTION

Figure 1:
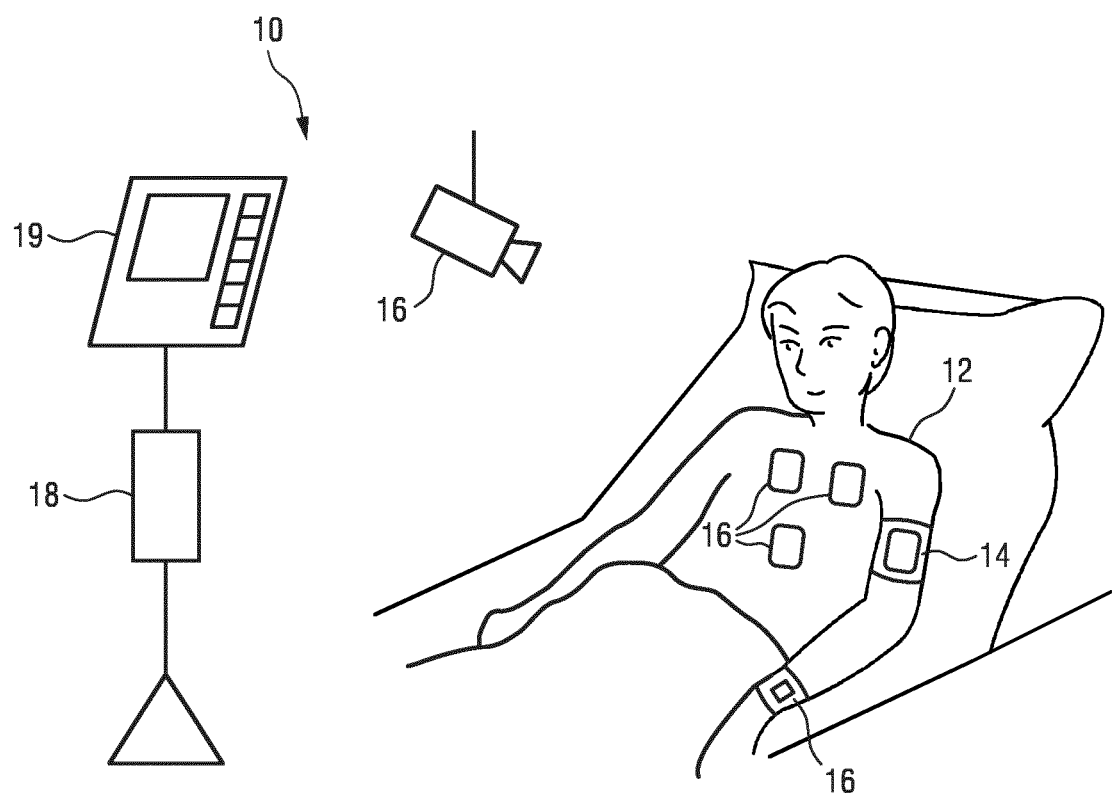
FIG. 1 shows a schematic illustration of an application scenario of a system for monitoring a patient according to an aspect of the present invention.

Patient monitoring in medium and low acuity settings is gaining more and more interest. In FIG. 1 the general concept of a system 10 for monitoring a patient 12 is illustrated. For instance, this may be a patient 12 in a clinical monitoring setting, such as a low acuity care setting who is continuously monitored or monitored based on spot checks. It may also be that a patient in a home care scenario or a person in a rehabilitation facility or a person in an elderly care unit etc. is monitored. Still further, it may be possible that a person in a fitness application (at home or in a studio etc.) is monitored.

In particular, a system 10 as illustrated in FIG. 1 may correspond to an early warning scoring (EWS) system in a hospital with which the health state of a patient is assessed by means of sensors 14, 16 and a health state of the patient is monitored. In the scenario of the present invention one sensor corresponds to a blood pressure measurement device 14. Based on the output of the sensors 14, 16, a health state parameter being indicative of the medical condition of the patient 12 is determined. An apparatus 18 according to the present invention is included in such a system 10 to provide a control signal for controlling the blood pressure measurement device 16.

Depending on the embodiment, the apparatus 18 may be in communication with the system 10 or may be integrated with the system 10. It is possible that the apparatus 18 includes the functionality of determining the health state of the patient 12. It is also possible that the apparatus 18 is in communication with a system that already provides information on the health state of the patient such as an existing EWS system in a hospital.

In most monitoring scenarios, one important parameter to be monitored is the blood pressure of a patient (systolic and/or diastolic and/or mean arterial blood pressure). A corresponding blood pressure measurement device is controlled based on operation settings. Depending on these operation settings, a measurement may result in a higher or lower comfort for the patient and provide a measurement of higher or lower precision. On the one hand, it is desired that the monitoring provides a sufficiently accurate assessment of the patient's condition. However, it is also desired that the measurement does not affect the patient comfort too much.

Figure 2:
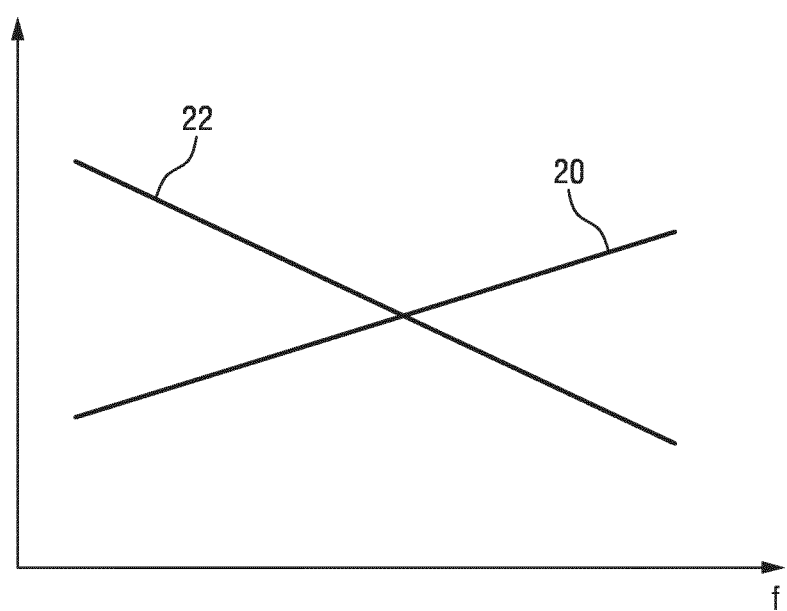
FIG. 2 shows a schematic illustration of a precision of a blood measurement and a patient comfort as function of a measurement frequency.

The present invention proposes to exploit this relationship between patient comfort and measurement precision of a blood pressure measurement. The operation settings based on which a blood pressure measurement device 14 is operated are chosen in view of the health state of the patient 12. This idea is illustrated based on an example in FIG. 2.

The diagram illustrates the precision 20 of a blood pressure measurement carried out on a patient as a function of a measurement frequency f, i.e. as a function of how often the blood pressure is actually measured. A higher measurement frequency results in a higher precision 20. Also, the patient comfort 22 is illustrated, which is also a function of the measurement frequency f. If the inflatable cuff is inflated and deflated at a higher frequency the patient is bothered more often and may suffer e.g. from pain or skin irritations caused by the inflatable cuff. The measurement precision 20 and the patient comfort 22 are usually reciprocal functions of operation parameters of a blood pressure measurement device. This applies to most operation settings of a blood pressure measurement device.

Turning back to FIG. 1, the blood pressure measurement device 14 may particularly correspond to a sphygmomanometer including an inflatable arm cuff. These devices provide a measurement based on compressing a limb of the patient with an external pressure applied by means of an inflatable cuff. This procedure is uncomfortable for the patient and may even hurt the patient. In particular, a blood pressure measurement carried out by means of a sphygmomanometer can result in pain caused by the inflation, in skin irritations under the inflatable cuff, in hematomas and/or in sleep disturbances if the measurement is conducted during the patient 12 is asleep. It is possible to control a sphygmomanometer to perform a measurement of lower precision, which less affects the comfort of the patient.

In the following, the idea of the present invention is described for a blood pressure measurement device being a sphygmomanometer for illustrative purposes. It is to be understood, however, that the concept of the present invention is not limited to sphygmomanometers but may also be applied with other blood pressure measurement principles, in particular non-invasive blood pressure measurement principles.

The operation settings of a sphygmomanometer may include parameters such as a measurement frequency, a maximum pressure up to which the inflatable cuff is inflated, a duration of the inflatable cuff being inflated, etc. On the one hand, these operation settings are related to the patient comfort. On the other hand, these operation settings are also related to a precision of a blood pressure measurement conducted based on these operation settings. A plurality of different embodiments are possible with respect to the operation settings, e.g. stopping a blood pressure measurement early, postponing it, deciding on inflation vs. deflation strategy, triggering by other parameters, etc. For instance, if the blood pressure of a patient is measured at a higher frequency, i.e. more often, the blood pressure can be monitored with a higher accuracy or precision. Also, if the inflatable cuff is kept inflated for a longer time period the validity of the measurement may be higher since more heartbeats of the patient can be detected. Furthermore, it is common to carry out a measurement of a systolic blood pressure (SBP) of the patient during cuff deflation. It is, however, also possible to obtain an SBP measurement of lower precision, i.e. with a higher standard deviation, from a measurement carried out during inflation of the cuff. Consequently, determining operation settings that correspond to a measurement being carried out during cuff inflation may also increase patient comfort. Further details with respect to how a blood pressure measurement can be carried out according to embodiments of the present invention are presented in the following.

The further vital sign sensors 16 may include a camera or another device for obtaining a signal being indicative of reflected light of a skin portion of the patient 12 and for deriving therefrom a heart rate, a blood oxygen saturation, a pulse rate, a respiration rate or an activity level may be included. Furthermore, the vital sign sensors may also include an SpO2 sensor to be applied, e.g., at the wrist or at a finger of the patient 12, for measuring the blood oxygen saturation, an accelerometer at an apex position of the patient 12 to detect a pulse rate, a respiration rate and/or a posture and activity information, a temperature sensor, an ECG sensor etc. The blood pressure measurement device 14 and the further vital sign sensors 16 may be in wired or wireless connection with the apparatus 18.

Usually, there is also provided a user interface 19 (e.g. a screen or a web page etc.) via which a user such as a physician, other medical personnel or the patient himself can interact with the system 10 and/or with the apparatus 18.

FIG. 3 illustrates an apparatus 18 for providing a control signal for a blood pressure measurement device 14 according to an aspect of the present invention in further detail. In particular, the apparatus 18 of the present invention may be in communication with an existing monitoring system 23 and rely upon a health state parameter determined in such a system.

In such a system a health state parameter of the patient is determined based on the signal of the blood pressure measurement device 14 and/or based on the signals of the further vital sign sensors. This health state parameter represents a measure for the condition of the patient. In particular, the health state parameter indicates whether the patient 12 is in a critical health condition and requires close surveillance or whether the condition of the patient 12 is uncritical and does not make it necessary that the patient is continuously monitored. Such a health state parameter may, e.g. include a risk score indicating the health state of the patient 12 on a predefined scale, such as a scale from 1 to 10 on which a score of 1 indicates an uncritical health state and a score of 10 indicates a critical state of the patient 12.

The apparatus 18 comprises an input interface 24 which is configured to obtain a health state parameter being indicative of the health state of the patient. This health state parameter then forms the basis for determining operation settings of a blood pressure measurement device 14 in a processing unit 28. These operation settings are related to the precision of a blood pressure measurement on the one hand and the patient comfort on the other hand.

The apparatus 18 further comprises a control interface 30 via which a control signal is provided to control the blood pressure measurement device 14 to perform a blood pressure measurement based on the determined one or more operation settings.

The apparatus 18 as illustrated in FIG. 3 may e.g. be incorporated into a blood pressure measurement device. Alternatively, it may be possible that the illustrated apparatus 18 is incorporated into a handheld device such as a smartphone or into a bedside monitor or the like.

In FIG. 4 another embodiment of the present invention is illustrated. The apparatus 18 is integrated into a monitoring system 10. In comparison to the above, the apparatus 18 additionally includes a health assessment unit 26 in which the health state of the patient 12 is determined. The input interface 24 is directly connected to the one or more of the vital sign sensors 16. The sensors provide one or more input signals. The input signals are evaluated in a health assessment unit 26 and a health state parameter is determined. This health state parameter then forms the basis for determining the operation settings in the processing unit 28.

This embodiment may correspond to the apparatus 18 being integrated with a hospital information system. For instance, the apparatus may partly or entirely be implemented in software running on a central server in a hospital.

In preferred embodiments it is possible that blood pressure measurement device 14 also forms part of the input sensors (as illustrated by the dashed lines in FIGS. 3 and 4), i.e. provides a signal which is used as an input for determining the health state parameter. Thus, an input signal being indicative of the systolic blood pressure of the patient can be used.

Preferably, the input interface is additionally configured to obtain an accuracy indicator being indicative of the accuracy or reliability of a respective input signal. For instance, a standard deviation of the sensor signal may be obtained.

In FIG. 5 an example for an early warning system scoring card 32 as used in an EWS system is illustrated. By means of such a card 32 a risk score can be determined based on different vital signs (heart frequency, blood pressure, breathing frequency and temperature). Also, further information such as whether the patient is conscious, whether he drinks enough etc. can be included. A score is derived from the different parameters by adding up the scores corresponding to different predefined ranges. For instance, a heart frequency of 105 will contribute one point to the risk score or a systolic blood pressure between 101 and 200 will not contribute any point. The risk score is determined by adding up the points or scores corresponding to the different vital signs and other parameters.

The risk score may correspond to the health state parameter that is used as the basis for determining the operation settings in the processing unit of the apparatus of the present invention.

The illustrated scoring card is used in a system for manual assessment (e.g. by a physician). It is possible that the risk score is determined and then provided to the apparatus of the present invention via the input interface (which could e.g. be implemented in the form of a smartphone app or a touchscreen or other interface on a blood pressure measurement device).

The same function may also be carried out automatically. In other words, a risk score representing a health state parameter may be determined based on a look-up table operation. This may, e.g. be carried out in the health assessment unit in the apparatus of the present invention. Different input signals are obtained, for each of the obtained input signals and the corresponding vital signs a look-up operation is carried out and an overall score is determined.

In other embodiments it may, however, also be possible that the health state parameter is determined by means of a function which allows directly deriving a score based on the at least one obtained input signal.

Based on such a risk score, the processing unit may, e.g. be configured to determining operation settings relating to a comparably lower precision but to a comparably higher patient comfort, as long as the determined risk score stays below 3.

In a preferred embodiment of the present invention, the operation settings are determined based on how the precision of the measurement actually affects a risk score being determined in the EWS. If it is determined based on the current health state parameter (e.g. the current blood pressure) that a measurement of higher precision does not at all affect a determined risk score, it is not required that a decrease in patient comfort is accepted.

Figure 6:
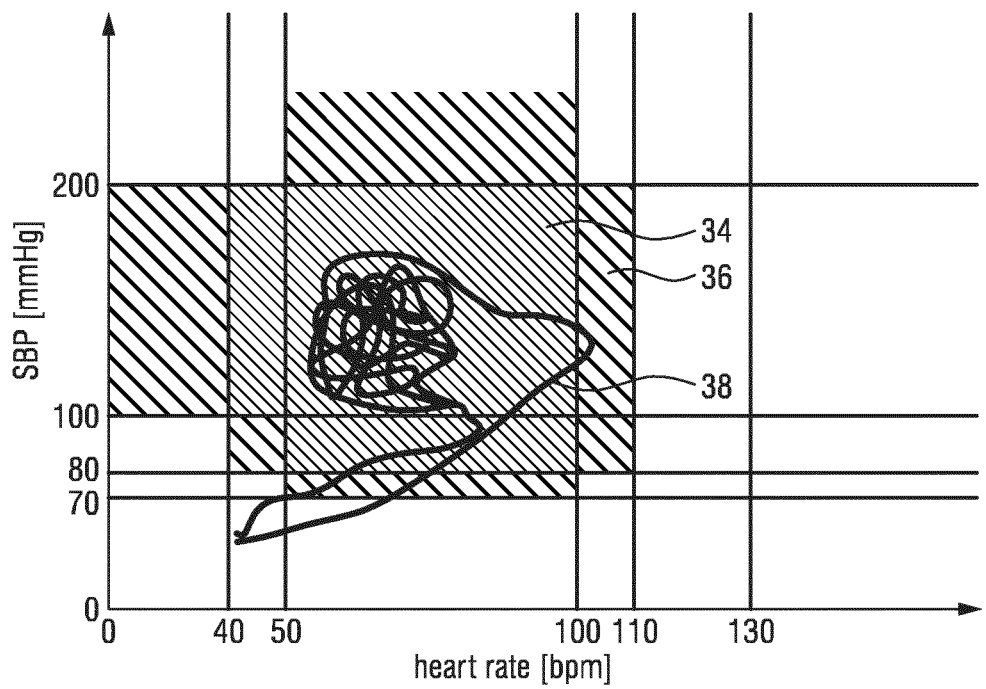
FIG. 6 shows an example of the assessment of a patient status in an early warning system based on a heart rate and a blood pressure of the patient.

In FIG. 6 a 2D representation of a patient status assessment is illustrated. The x-axis represents the heart rate of the patient. The y-axis represents the SBP of the patient. The health state of the patient can be defined as a function of the two vital signs. As illustrated in FIG. 6, there may be a safe zone 34 which indicates that the patient is currently not at risk. There may further be an increased risk zone 36 indicating a higher risk for a deteriorating health state of the patient. If the function 38 moves out of the safe zone 34 and the increased risk zone 36 this indicates a shock state of the patient. In terms of the present invention the different zones can be considered to correspond to the values of the health state parameter. Thereby, it is possible to use the actually measured systolic blood pressure or an estimated systolic blood pressure.

Figure 7:
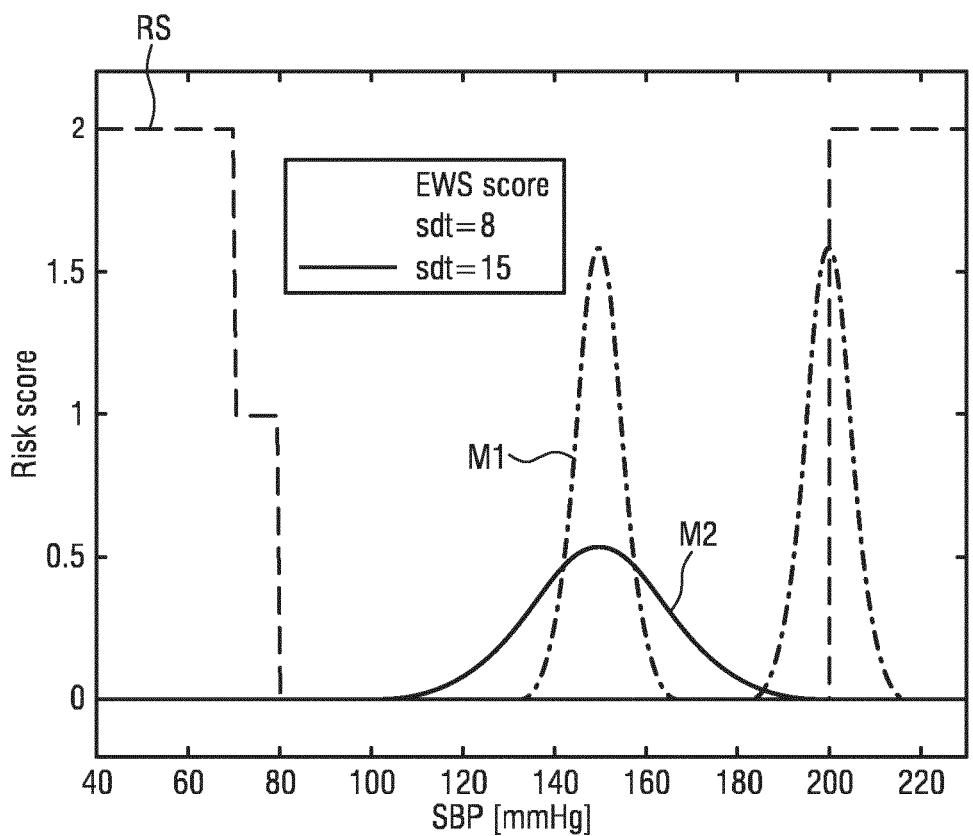
FIG. 7 illustrates an example for probability densities of blood pressure measurements carried out with different precisions and their influence on an early warning system.

One approach to capture the precision of a blood pressure measurement conducted with the blood pressure measurement device is to consider the standard deviation. In FIG. 7 the impact of a measurement precision of the blood pressure measurement device for assigning a risk score RS (corresponding to a health state parameter or forming an input signal based on which a health state parameter is determined) is illustrated. It is illustrated that the risk score RS is a function of the SBP. Further, two simulated measurements M1 and M2 are shown with their probability densities. It can be seen that measurement M2 has a different precision, i.e. a higher standard deviation, than measurement M1. Both have the same mean. Measurement M1 may be the output of a blood pressure measurement device operated based on a first set of operation settings. Measurement M2 may be the output of a blood pressure measurement device operated based on a second set of operation settings.

Both measurements M1 and M2 cover with their probabilities the risk score of zero. In this situation, a risk score of zero could be assigned to both measurements although the measurement precision is different. However, if the systolic blood pressure is around 200 mmHg the different precision becomes more important. The average reported risk score for a plurality of systolic blood pressure measurements with a given inherent precision and for a specific scoring system may be defined by integrating a known or assumed probability distribution of a systolic blood pressure measurement with the risk score according to:

$$Score_{SBP} = \int_0^{Max} \rho_{SBPmeas} EWS(SBP) dSBP \quad (1)$$

If this definition is used a risk score for systolic blood pressure measurements of different precisions may be calculated.

Figure 8:
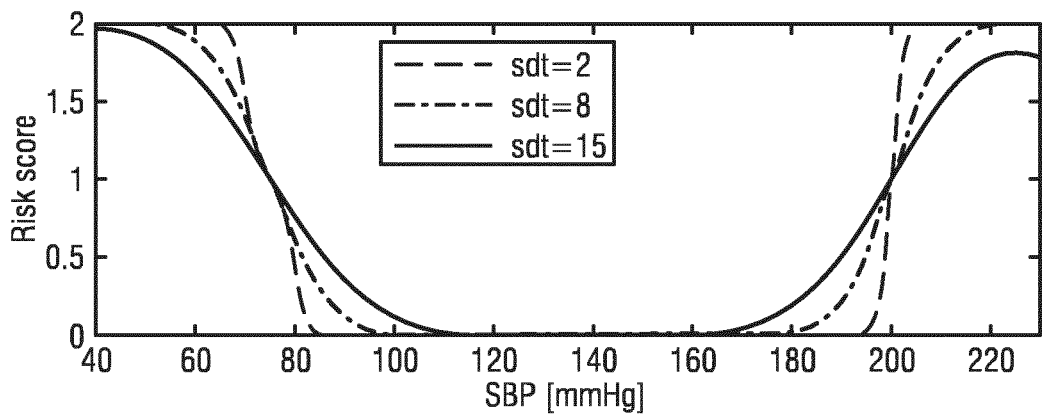
FIG. 8 schematically illustrates an average early warning system risk score as a function of a measured blood pressure with varying precision.

FIG. 8 illustrates an average systolic blood pressure measurement risk score calculated for different precisions (standard deviations) based on the above-indicated equation. It can be seen that in order to reproduce the risk score as close as possible a very high precision with a standard deviation of 2 mmHg is required for systolic blood pressure values measured in ranges around where the EWS score changes. It should be noted that current non-invasive blood pressure measurements have a precision of about 8 mmHg as illustrated in FIG. 8. This line can be used as a benchmark for improved methods for adapting the measurement precision of a blood pressure measurement.

Thus, in other words, according to the present invention it becomes possible that a health state parameter (which actually corresponds to the SBP in the illustrated example in FIG. 7) is used as input for determining operation settings (that define the precision of a measurement, i.e. the standard deviation illustrated in FIG. 7). In order to provide an accurate risk score, it is required that a measurement of higher precision is carried out (i.e. corresponding operation settings are determined) as long as the SBP is around 80 mmHg or around 200 mmHg. If the SBP is between 120 and 160 there is no need for a higher precision since the risk score will be zero for a measurement of higher precision as well as for a measurement of lower precision.

Figure 9:
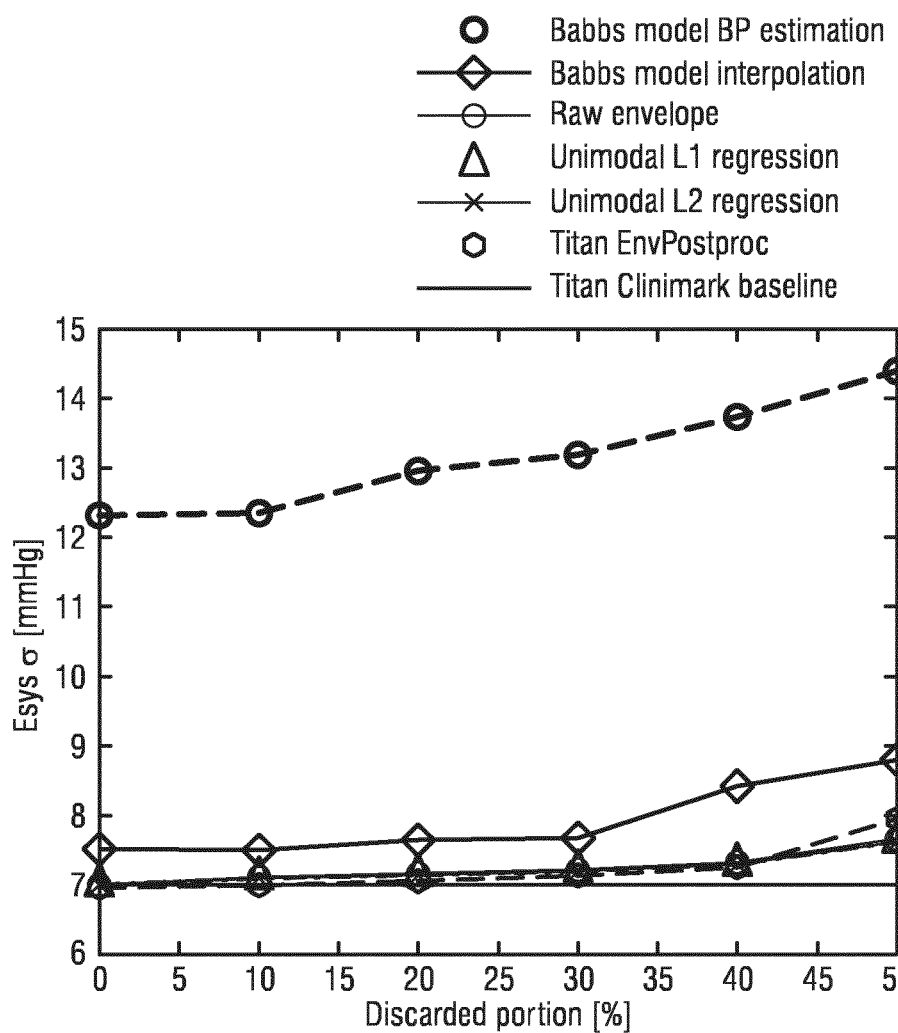
FIG. 9 schematically illustrates an example for a resulting precision as determined by means of different models as a function of a number of discarded sampling points of a blood pressure measurement.

One option for adapting the precision of a blood pressure measurement obtained by means of a sphygmomanometer is to take into account less pulses when creating a signal envelope. This is illustrated in FIG. 9, in which the detected pulses during a measurement are successively removed. The SBP is inferred by different state-of-the-art algorithms. It can be seen that the precision of the measurement decreases when a higher portion of sampling points is discarded for all different algorithms. Again, the precision is expressed in terms of the standard deviation of the measurement (indicated on the y-axis). Thus the operation settings may reflect that less pulses are to be taken into account.

Figure 10:
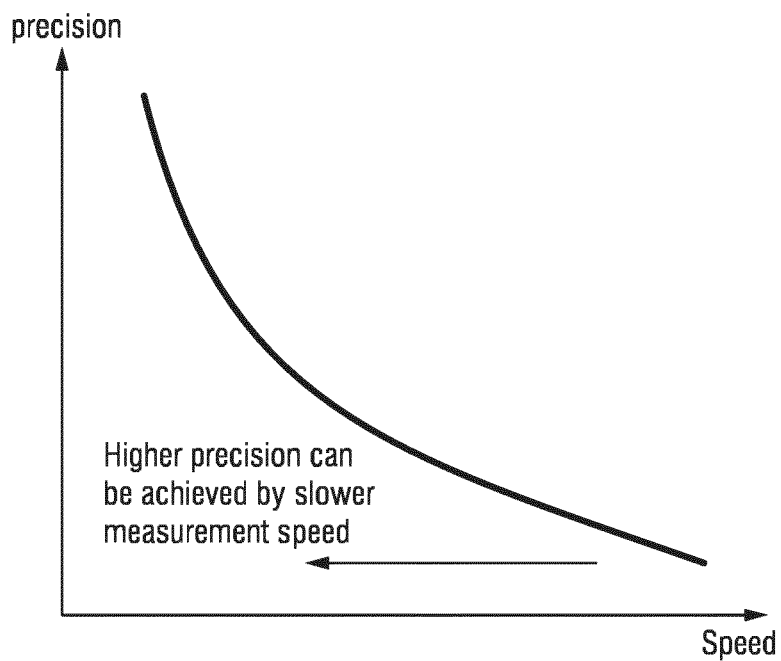
FIG. 10 schematically illustrates the relation of the precision of a blood pressure measurement and the measurement speed.

The procedure of discarding sampling points corresponds to inflating or deflating the inflatable cuff at a higher speed dependent on the heart rate of the patient. If fewer pulses are detected, the measurement precision decreases. If 50% of the pulses are discarded during a measurement, a 50% shorter measurement duration is achieved. The general relation of the measurement precision versus the measurement speed is illustrated in FIG. 10.

Another option is to increase the measurement precision by including an additional pulse detection method such as a photoplethysmography measurement as shown in Nitzan et al., "Automatic Non-Invasive Measurement of Systolic Blood Pressure using Photoplethysmography", 2009 and Nitzan et al., "Comparison of Systolic Blood Pressure Values Obtained by Photoplethysmography and by Korotkoff Sounds", Sensors 2013. According to the present invention it is possible to make use of different input signals being indicative of one or more vital signs of the patient.

Based on the above-outlined insights it is therefore possible to adapt the precision of a blood pressure measurement albeit keeping a similar EWS notification performance at improved patient comfort, e.g. by reducing the measurement duration if the SBP is expected to be in a certain range. In other words, adaptive context-specific blood pressure measurement precisions are used to keep a similar EWS notification performance at improved patient comfort e.g. by reduced measurement duration if the SBP will be or is expected to be in a certain range.

In particular, three approaches for obtaining a blood pressure measurement of the systolic blood pressure are presented in the following. These approaches can be defined by means of corresponding operation settings.

1.) The SBP can be inferred during cuff inflation by continuously inferring SBP from envelope extrapolation. Inflation is stopped when the SBP value with sufficient precision can be inferred related to a predefined acceptance level for EWS score notification performance. If required the process can be adapted, e.g., by switching to deflation measurement mode if arrhythmias result in an SBP measurement with insufficient precision and accuracy or by deflating immediately and repeating the measurement in a modus providing a higher accuracy and precision.

2.) The SBP can be inferred from a calculation based on a diastolic blood pressure (DBP) and a mean arterial blood pressure (MBP) extracted from a signal envelope during inflation. The SBP can be calculated based on SBP=3 MBP−2 DBP and ASBP=3ΔMBP+2 ΔDBP. This formula can be adapted by patient characteristics such as age and gender. Such parameters may be included in the medical record data. SBP precision can be estimated from the precisions of AMBP and ADBP determined during cuff-inflation. Again, the process can be adapted, e.g., by switching to deflation measurement mode if arrhythmias (also indicated by the health state parameter) result in an SBP measurement with insufficient precision and accuracy or by deflating immediately and repeating the measurement in a modus providing a higher accuracy and precision.

As a variant, it is also possible to determine operation settings resulting in that the DBP is measured by means of a cuff-based blood pressure measurement method (e.g. by the auscultatory method) whereas the MBP is inferred based on a surrogate measure. In this embodiment, maximal cuff pressure is reduced as well as measurement time, which results in a significantly improved patient comfort.

3.) It is possible to automatically adapt the blood pressure measurement accuracy/precision (i.e. provide corresponding operation settings) if previously reported blood pressure measurements or a blood pressure surrogate (health state parameter) indicate a change in patient status. For instance a higher accuracy/precision may be required if previously acquired blood pressure measurements indicate a decreasing/increasing blood pressure.

In a first variant additional information on the patient status can be obtained from complementary sensors or sensor systems providing one or more input signals such as a sensor at the lower chest measuring Pulse, Respiration Rate, activity or a photoplethysmography sensor for measuring (SpO2, Pulse).

Figure 11:
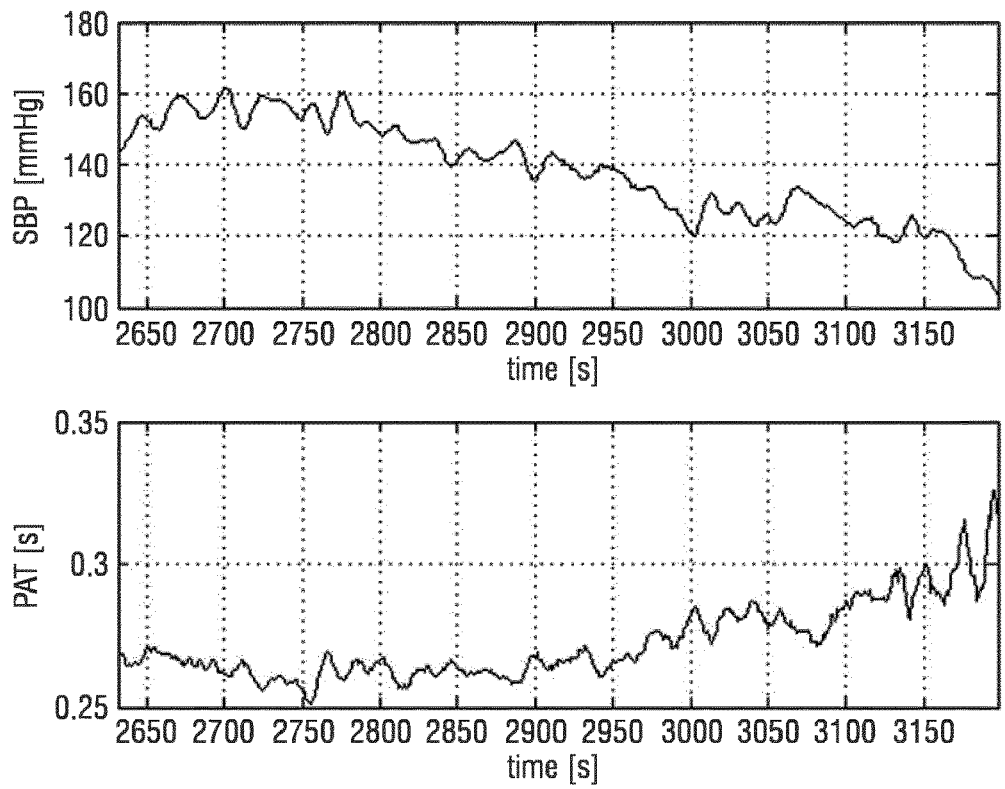
FIG. 11 schematically illustrates an example of decreasing blood pressure indicated by an increasing pulse arrival time representing a blood pressure measurement surrogate.

In another variant information from a BP surrogate such as Pulse Transit Time (PTT) or Pulse Arrival Time (PAT), morphology features from photoplethysmography (PPG) or alike may indicate a stable/unstable/critical trend in the patient's health state which may be used as a basis for adapting the blood pressure measurement performance. In FIG. 11 an example for an increasing PAT (lower diagram) is shown that indicates a decreasing SBP (upper diagram). This can be taken into account for determining operation settings for the blood pressure measurement (which is probably required to be a blood pressure measurement of higher measurement precision).

As shown in FIG. 11, a decreasing SBP (upper diagram) is indicated by a SBP surrogate (lower diagram, here PAT is shown). The PAT increases within the time interval from 2900 s to 3100 s by about 20 ms which indicates a trend of a significant SBP decrease of 20 mmHg. This PAT change is used to adapt the precision of the next blood pressure measurement (i.e. as an input signal when determining the operation settings for the next blood pressure measurement). The required blood pressure precision may be estimated from a look-up table or a functional relationship. Alternative blood pressure surrogates e.g. derived from PPG only, can also be used.

Alternatively, the change in the BP surrogate can be used to estimate MBP whereas DBP is measured by a cuff-based measurement method (e.g. by the auscultatory method). Then, SBP can be inferred from MBP and DBP as discussed above. In this embodiment, maximal cuff pressure is reduced as well as measurement time, which results in a significantly improved patient comfort.

Figure 12:
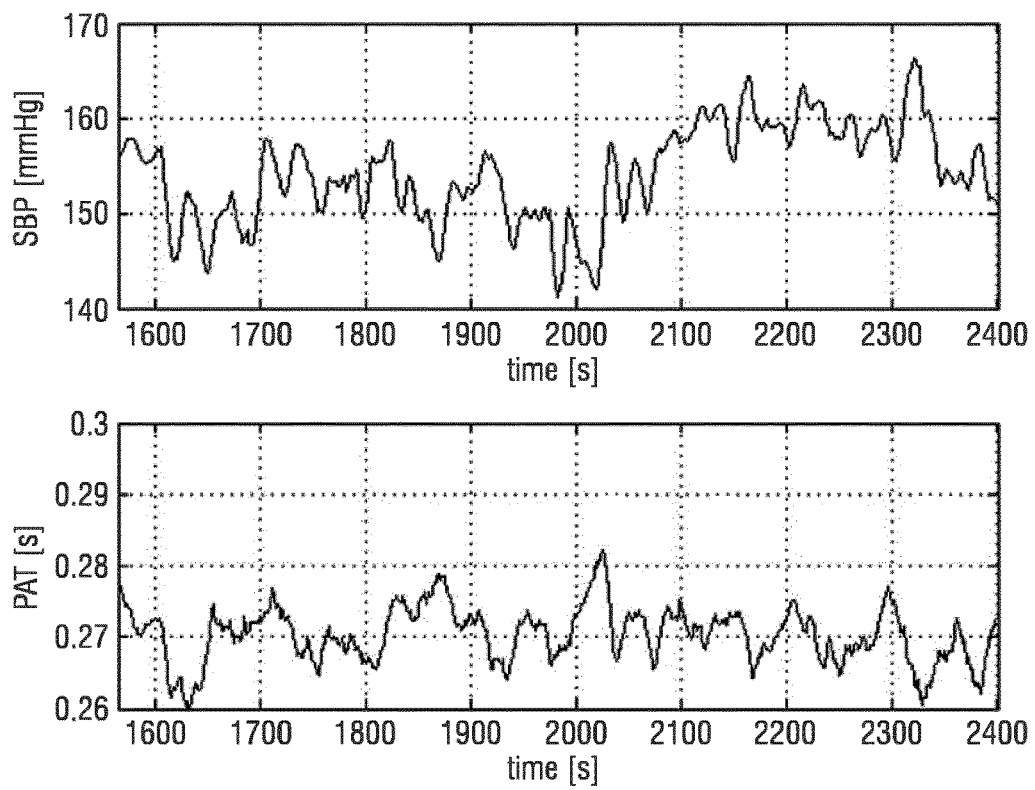
FIG. 12 schematically illustrates a blood pressure measurement of a patient during a continuous monitoring period and a pulse arrival time representing a surrogate blood pressure measurement.

Further alternatively, as illustrated in FIG. 12, if the SBP measurement surrogate PAT (lower diagram) indicates no or only small changes in patient status (corresponding to a health state parameter) compared to previous blood pressure measurements, operation settings can be determined that are related to a higher measurement speed or a specific measurement modus. In the upper diagram the SBP change of a patient during a continuous monitoring period is illustrated. In the lower diagram the PAT as SBP surrogate measurement changes. In this example, the SBP remains at 150 mmHg, which translates—in terms of the EWS score—to a score of 0. The PAT as SBP surrogate remains in a band of 270 ms (±10 ms) indicating a stable SBP.

4.) A precision map based on a hospital-specific EWS scoring system can be defined to adapt blood pressure measurements precision to optimize patient comfort. EWS scoring systems vary between hospitals and a hospital can adapt blood pressure measurement speed vs. patient comfort to his particular situation. A hospital may specify a certain policy and provide a corresponding protocol parameter. For that purpose, a system and method is described to adapt the blood pressure measurement precision vs. patient comfort for a specific EWS scoring system in a hospital.

Figure 13:
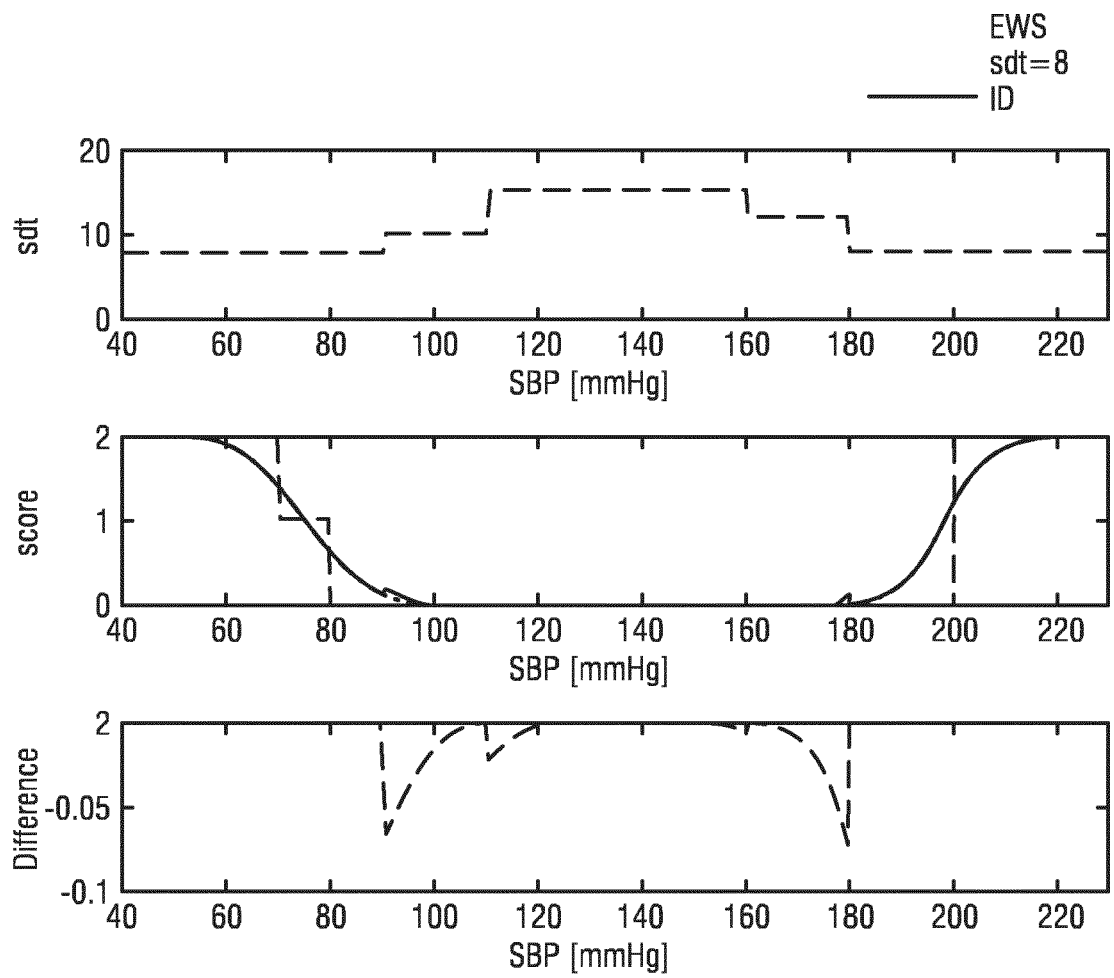
FIG. 13 schematically illustrates a method to adapt the precision of a blood pressure measurement to a specific early warning system scoring system.

In the upper diagram in FIG. 13 an example for a method for adapting blood pressure measurement precision to a specific EWS scoring system is illustrated. The required measurement is a function of the SBP value (upper diagram). A lower precision is required in a range of low patient risk (as indicated by the health state parameter). The standard deviation is dependent on the SBP. This can be chosen according to the needs of a hospital or a particular patient. In the middle diagram the reported average EWS scores for a fixed precision of 8 mmHg (dashed lined) and for the adapted precision (dashed dotted line), i.e. using the sdt from the upper diagram, are presented. The difference in performance (constant sdt−adapted sdt) of the reported EWS score is illustrated in the lower diagram. Obviously, there is some performance decrease due to the adaptive precision as proposed herein. However this reduction can be quantified and a hospital can decide on an appropriate implementation. The performance decrease can be balanced by a higher patient comfort due to faster SBP measurement. This knowledge can be introduced into the apparatus or system of the present invention by means of a protocol parameter specifying the measurement precision (represented by the standard deviation) as a function of the health state parameter (corresponding to the SBP) as illustrated in the upper diagram.

Figure 14:
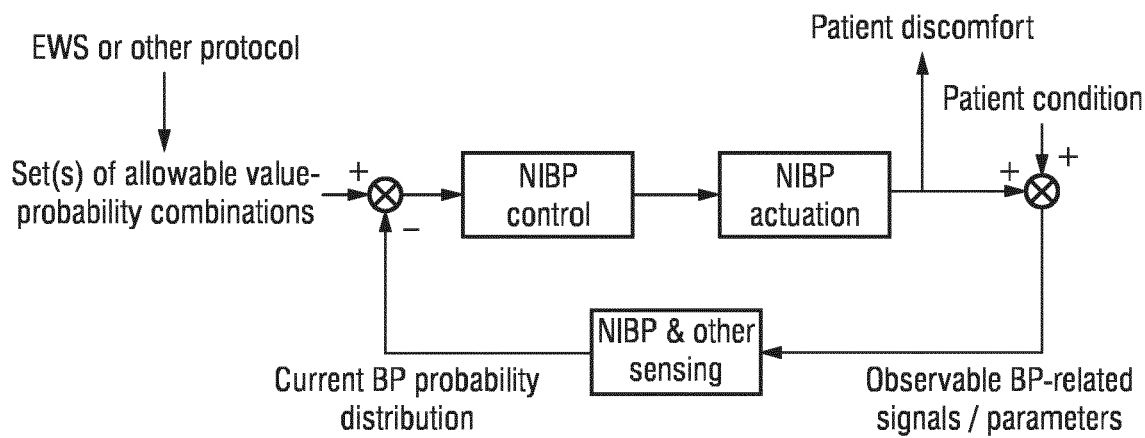
FIG. 14 schematically illustrates the concept to adapt the precision of the blood pressure measurement based on a protocol parameter.

In FIG. 14 the generalized concept to adapt the blood pressure measurement based on the actual EWS protocol being in use taking into account measures of patient discomfort and patient conditions. The automated continuous optimization of measurement accuracy/precision vs. patient comfort can be regarded as a control loop. The error signal feeding into the controller is the difference between the actual/current BP probability distribution and whatever the protocol allows such distributions to be (e.g. the protocol as represented by a protocol parameter could allow up to 10% probability of SBP>160 mmHg as long as the probability of 160 mmHg>SBP>90 mmHg is at least 85%, and so on). Based on the error signal (corresponding to the accuracy indicator), the controller determines if and when and how any blood pressure actuation (e.g. pump, valve actuation) is done, i.e. determines appropriate operation settings. When the blood pressure actuation is changed both the observability of the patient's condition as well as the patient's comfort are affected. Current BP probability distribution is derived from the sensed blood pressure signals but also possibly other input signals (e.g. signals representing PTT, HR, etc.).

Note that this system realizes the envisioned optimization in principle by controlling towards a minimally required blood pressure actuation. Depending on the health state and accuracy parameter, operation settings are determined that relate to the minimum required precision (and the maximum possible patient comfort). In practice, some damping and/or delay may be needed to deal with noise in the sensing part (make the loop stable).

It is thus possible to also use a protocol parameter as an input. This protocol parameter may be obtained via the input interface. This protocol parameter may indicate a treatment policy and may be included for determining the one or more operation settings. For instance, such a protocol parameter may indicate that a blood pressure measurement is to be carried out during cuff inflation only if the patient is considered to be in an uncritical health state. This may be the case if the patient has a risk score of lower than 3. This protocol parameter may be provided by a physician for a particular patient or may represent a general treatment policy as defined for a care facility based on a long-term study etc.

In another embodiment of the present invention it may also be possible that the input interface is configured to also obtain medical record data of the patient in addition to the at least one input signal. Such medical record data may correspond to a medical history of the patient. For instance, a patient having a medical history of epilepsy or other medical conditions may require to be constantly monitored with high precision in spite of his vital signs indicating that he is in an uncritical state at the moment. The medical record data allows determining the health state parameter also based on such prior knowledge. Then, appropriate operation settings may be determined.

Figure 15:
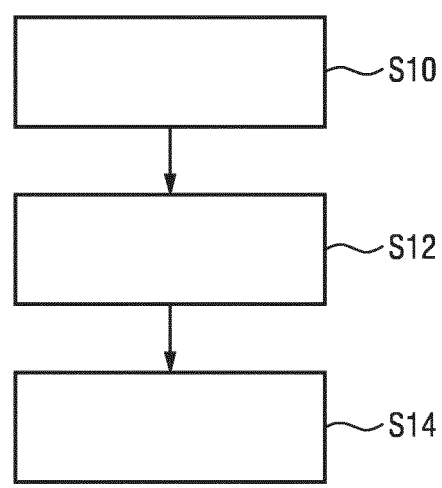
FIG. 15 schematically illustrates a method according to an aspect of the present invention.

In FIG. 15 a method according to an aspect of the present invention is illustrated. The method comprises the steps of obtaining S10 a health state parameter based thereupon, determining S12 one or more operation settings of a blood pressure measurement device based on the health state parameter and providing S14 a control signal for a blood pressure measurement device to perform a blood pressure measurement based on said one or more operation settings.

A method according to the present invention may, e.g., be carried out by a processor. This processor may, e.g., be integrated into an early warning system for use in a hospital or general ward environment.

In embodiments of the present invention it is possible that the input interface is configured to obtain at least on health state parameter. A health state parameter can be represented by a risk score. A health state parameter can also be represented by a vital sign signal.

As used herein a blood pressure measurement device may particularly be represented by a non-invasive blood pressure measurement device, in particular a sphygmomanometer. However, it may be possible that the idea underlying the present invention is exploited with other types of devices and other measurement principles.

The apparatus of the present invention may be incorporated into a blood pressure measurement device. The apparatus of the present invention may also be incorporated into a patient monitoring system or into a network-based hospital information system. It may also be possible that the apparatus of the present invention is incorporated in other forms.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for providing a control signal for a blood pressure measurement device, comprising:

an input interface configured to obtain a health state parameter being indicative of a health state of a patient, said health state parameter including a risk score indicating the health state of the patient on a predefined scale and being determined based on a blood pressure measurement of the patient;

a processor configured to determine one or more operation settings of a blood pressure measurement device based on the health state parameter, said one or more operation settings including a parameter that can be adjusted at the blood pressure measurement device when conducting a blood pressure measurement with the blood pressure measurement device and that affects a precision of said blood pressure measurement and a patient comfort resulting from said blood pressure measurement, wherein the one or more operation settings are determined based on whether the risk score is unaffected by a blood pressure measurement of a first precision level and whether the risk score is affected by a blood pressure measurement of a second precision level; and a controller configured to provide a control signal for the blood pressure measurement device to perform a blood pressure measurement based on said one or more operation settings.

2. The apparatus as claimed in claim 1, wherein:
the controller is configured to provide the control signal for a sphygmomanometer comprising an inflatable cuff configured to be applied to a limb of the patient and a pressure sensor for providing a pressure signal being indicative of the pressure in the inflatable cuff; and
the processor is configured to determine the one or more operation settings including at least one of a parameter being indicative of a maximum pressure in the inflatable cuff during a measurement, a parameter being indicative of a duration of the inflatable cuff being inflated during a measurement, a parameter being indicative of an integral of the pressure applied during a measurement and a parameter being indicative of a number of heartbeats to be detected.

3. The apparatus as claimed in claim 1, wherein the processor is configured to:
determine the one or more operation settings related to the first precision level and a first patient comfort level when the health state parameter indicates an uncritical health state of the patient; and
determine the one or more operation settings related to the second precision level and a second patient comfort level when the health state parameter indicates a deteriorating health state of the patient, wherein the first precision level is lower than the second precision level and the first patient comfort level is higher than the second patient comfort level.

4. The apparatus as claimed in claim 3, wherein said risk score being below a predefined threshold indicates the uncritical health state of the patient and said risk score being above said predefined threshold indicates the deteriorating health state of the patient.

5. The apparatus as claimed in claim 3, wherein:
the controller is configured to provide the control signal for a sphygmomanometer comprising an inflatable cuff configured to be applied to a limb of the patient and a pressure sensor for providing a pressure signal being indicative of the pressure in the inflatable cuff; and
the processor is configured to determine the one or more operation settings being related to said second precision level and said second patient comfort level by resulting in a systolic blood pressure of the patient being inferred based on an auscultatory or an oscillometric method during deflation of the inflatable cuff.

6. The apparatus as claimed in claim 3, wherein:
the controller is configured to provide the control signal for a sphygmomanometer comprising an inflatable cuff configured to be applied to a limb of the patient and a pressure sensor for providing a pressure signal being indicative of the pressure in the inflatable cuff; and
the processor is configured to determine the one or more operation settings being related to said first precision level and said first patient comfort level by resulting in a systolic blood pressure of the patient being inferred based on at least one of:
extrapolation of a signal envelope of the pressure signal during cuff inflation;
extraction of a diastolic blood pressure and a mean arterial blood pressure from a signal envelope of the pressure signal during cuff inflation; and
extraction of a diastolic blood pressure from a signal envelope of the pressure signal during cuff inflation and extraction of a mean arterial blood pressure from a vital sign of the patient corresponding to a surrogate blood pressure measurement of the patient derived from at least one additional signal comprising a photoplethysmography signal and/or an electrocardiogram.

7. The apparatus as claimed in claim 1, wherein the input interface is configured to obtain at least one input signal indicative of a vital sign of a patient, said apparatus further configured to determine a health state parameter indicative of the health state of the patient based on the at least one input signal.

8. The apparatus as claimed in claim 7, wherein the input interface is configured to:
obtain the at least one input signal from the blood pressure measurement device, said the at least one input signal being indicative of a blood pressure of the patient; and/or
obtain the at least one input signal and a corresponding accuracy indicator being indicative of a validity of the at least one input signal with respect to the vital sign, said accuracy indicator being predefined for a respective input signal or being updated continuously based on a current blood pressure measurement.

9. The apparatus as claimed in claim 8, wherein at least one of:
the processor is configured to determine the one or more operation settings based on said at least one input signal and said corresponding accuracy indicator; and
the apparatus is configured to determine the health state parameter based on said at least one input signal and said corresponding accuracy indicator.

10. The apparatus as claimed in claim 7, wherein:
the input interface is configured to obtain medical record data of the patient in addition to the at least one input signal, said medical record data being indicative of a medical history of the patient; and
the apparatus is configured to determine the health state parameter based on the medical record data of the patient in addition to the at least one input signal.

11. The apparatus as claimed in claim 7, wherein the input interface is configured to obtain the at least one input signal being indicative of a blood pressure, a blood oxygen saturation, a body temperature, a concentration of carbon dioxide in the respiratory gases, a heart rate, a pulse arrival time, a pulse transit time, a pulse morphology and a breathing frequency of the patient.

12. The apparatus as claimed in claim 7, wherein the input interface is configured to obtain a protocol parameter in addition to the at least one input signal, said protocol parameter being indicative of a predefined treatment policy; and
the processor is configured to determine the one or more operation settings based on said at least one input signal and said protocol parameter.

13. A system for monitoring a patient, comprising:
at least one vital sign sensor configured to provide at least one input signal being indicative of a vital sign of the patient;
the apparatus as claimed in claim 1, wherein the apparatus is configured to determine a health state parameter being indicative of a health state of the patient based on the at least one input signal;
a blood pressure measurement device configured to conduct a blood pressure measurement on the patient; and
an interactive display configured to display the determined health state parameter and/or a blood pressure of the patient to a user.

14. A method for providing a control signal for a blood pressure measurement device, comprising steps of:

obtaining a health state parameter being indicative of a health state of a patient, said health state parameter including a risk score indicating the health state of the patient on a predefined scale and being determined based on a blood pressure measurement of the patient;

determining one or more operation settings of a blood pressure measurement device based on the health state parameter, said one or more operation settings including a parameter that can be adjusted at the blood pressure measurement device when conducting a blood pressure measurement with the device and that affects a precision of said blood pressure measurement and a patient comfort resulting from said blood pressure measurement, wherein the one or more operation settings are determined based on whether the risk score is unaffected by a blood pressure measurement of a first precision level and whether the risk score is affected by a blood pressure measurement of a second precision level; and providing a control signal for the blood pressure measurement device to perform a blood pressure measurement based on said one or more operation settings.

15. A non-transitory computer readable medium comprising program code for causing a computer to:

obtain a health stare parameter being indicative of a health state of a patient, said health state parameter including a risk score indicating the health state of the patient on a predefined scale and being determined based on a blood pressure measurement of the patient;

determine one or more operation settings of a blood pressure measurement device based on the health state parameter, said one or more operation settings including a parameter that can be adjusted at the blood pressure measurement device when conducting a blood pressure measurement with the blood pressure measurement device and that affects a precision of said blood pressure measurement and a patient comfort resulting from said blood pressure measurement, wherein the one or more operation settings are determined based on whether the risk score is unaffected by a blood pressure measurement of a first precision level and whether the risk score is affected by a blood pressure measurement of a second precision level; and provide a control signal for the blood pressure measurement device to perform a blood pressure measurement based on said one or more operation settings.

* * * * *